US007907170B2

(12) United States Patent
Watanabe

(10) Patent No.: US 7,907,170 B2
(45) Date of Patent: Mar. 15, 2011

(54) ELECTRONIC ENDOSCOPE

(75) Inventor: Yasuharu Watanabe, Kanagawa (JP)

(73) Assignee: Hoya Corporation, Tokyo (JP)

( * ) Notice: Subject to any disclaimer, the term of this patent is extended or adjusted under 35 U.S.C. 154(b) by 1345 days.

(21) Appl. No.: 11/365,506

(22) Filed: Mar. 2, 2006

(65) Prior Publication Data
US 2006/0198620 A1   Sep. 7, 2006

(30) Foreign Application Priority Data

Mar. 2, 2005   (JP) .............................. P2005-056979

(51) Int. Cl.
*A62B 1/04*   (2006.01)
(52) U.S. Cl. .......................... 348/65; 348/68; 348/220.1
(58) Field of Classification Search ................ 348/220.1
See application file for complete search history.

(56) References Cited

U.S. PATENT DOCUMENTS

| 5,436,657 A * | 7/1995 | Fukuoka .................... 348/231.4 |
| 6,059,722 A | 5/2000 | Matumoto et al. |
| 6,078,353 A | 6/2000 | Yamanaka et al. |
| 6,540,671 B1 * | 4/2003 | Abe et al. ...................... 600/180 |
| 6,629,925 B2 | 10/2003 | Kurosawa et al. |
| 7,324,136 B2 | 1/2008 | Kubo |
| 7,573,504 B2 * | 8/2009 | Takane ....................... 348/220.1 |
| 2002/0196348 A1 * | 12/2002 | Kubo ........................ 348/220.1 |
| 2005/0220447 A1 | 10/2005 | Ito |
| 2006/0082845 A1 | 4/2006 | Watanabe |

FOREIGN PATENT DOCUMENTS

| JP | 62-156613 | 7/1987 |
| JP | 62-201411 | 9/1987 |
| JP | 1-107732 | 4/1989 |
| JP | 6-254045 | 9/1994 |
| JP | 9-090244 | 4/1997 |
| JP | 11008836 A * | 1/1999 |
| JP | 11-216107 | 8/1999 |
| JP | 11-216108 | 8/1999 |
| JP | 11-216109 | 8/1999 |

(Continued)

OTHER PUBLICATIONS

English Language Abstract of family member JP Laid-open Patent Publication No. HEI 10-118019, May 12, 1998.

(Continued)

*Primary Examiner* — Jason Chan
*Assistant Examiner* — Cynthia Calderon
(74) *Attorney, Agent, or Firm* — Greenblum & Bernstein, P.L.C.

(57) ABSTRACT

An electronic endoscope has a light source that radiates illuminating light, a movie-image processor, a still-image processor, an image-change processor, and provisional image displayer. The still-image processor that alternately reads odd-line image-pixel signals and even-line image-pixel signals over two field interval to generate a still image on the basis of one frame worth of image-pixel signals generated by a one-time still image exposure. The illuminating light being blocked for a latter filed interval in the two field interval. The image change processor switches between a performance of the movie-image processor for displaying the movie-image and a performance of the still-image processor for displaying the still-image. While the still-image processor reads the odd-line and even-line image-pixel signals over the two field intervals, the provisional image displayer displays a provisional image on the basis of at least one of odd-field image-pixel signals and even-field image-pixel signals, which are obtained by an exposure before the still image exposure.

5 Claims, 5 Drawing Sheets

FOREIGN PATENT DOCUMENTS

| | | |
|---|---|---|
| JP | 11-225955 | 8/1999 |
| JP | 2001-045473 | 2/2001 |
| JP | 2002-051977 | 2/2002 |
| JP | 3370871 | 11/2002 |
| JP | 2003-008948 | 1/2003 |
| JP | 3398550 | 2/2003 |

OTHER PUBLICATIONS

English Language Abstract of family member JP Laid-open Patent Publication No. HEI 10-85175, Apr. 7, 1998.

* cited by examiner

ELECTRONIC ENDOSCOPE

BACKGROUND OF THE INVENTION

1. Field of the Invention

The present invention relates to an electronic endoscope having a video-scope and a video-processor, especially, it relates to a signal process for displaying an observed image while recording a still image.

2. Description of the Related Art

In an electronic endoscope, an interline-transfer (IT) CCD is used to display a movie image on a monitor, wherein odd-field image-pixel signals and even-field image-pixel signals are alternately read from the CCD for one-field reading interval. When displaying or recording a still image generated by a one-time exposure, a shading or blind member is driven so as to block light that is emitted from a lamp and directed to an object, for a one-field reading interval. Thus, odd-line image-pixel signals and even-line image pixel signals are read from the CCD in order, for one-frame (two-field) reading interval, so that a high-quality still image is obtained without a blur.

SUMMARY OF THE INVENTION

An object of the present invention is to provide an electronic endoscope system that is capable of smoothly and continuously displaying an observed image without an interruption of an image-display while recording a still image.

An electronic endoscope according to the present invention has a light source that radiates illuminating light, a movie-image processor, and a still-image processor. The movie-image processor alternately reads odd-field image-pixel signals corresponding to an odd-field and even-field image-pixel signals corresponding to an even-field to generate a movie-image. For example, one field worth of image-pixel signals is temporarily stored in a memory as image data and is updated in each filed interval. The still-image processor that alternately reads odd-line image-pixel signals and even-line image-pixel signals over two field interval to generate a still image on the basis of one frame worth of image-pixel signals generated by a one-time exposure (herein, designated as "still-image exposure"). The illuminating light being blocked for a latter filed interval in the two field interval. For example, blocking member such as a chopper is applied. As for an adjustment of an exposure-time, for example, a rotary shutter that has an aperture and a shading portion are provided. The aperture and the shading portion are formed so as to alternately pass and block the illuminating light, and that rotates so as to adjust an exposure-time.

The electronic endoscope has further has an image change processor and a provisional image displayer. The image change processor switches a performance of the movie-image processor for displaying the movie-image and a performance of the still-image processor for displaying the still-image. For example, a switch button for displaying and/or recording a still image is provided on the video-scope. While the still-image processor reads the odd-line and even-line image-pixel signals over the two field intervals, the provisional image displayer displays a provisional image on the basis of at least one of odd-field image-pixel signals and even-field image-pixel signals, which are obtained by an exposure before the still image exposure, namely, the one-time exposure for recording a still image.

While the odd-line and even-line image-pixel signals are read over the two field interval, the observed image is displayed regardless of the block of the illuminating light. Therefore, a blank interval wherein the observed image is not displayed and a screen becomes black does not occur, and the operator can properly continue a work such as an operation using an electronic endoscope when recording a still image.

To display the provisional image by adjusting an update-timing, for example, the provisional image displayer changes an update interval of the image data from one field interval to two field intervals when the performance of the still image processor is started. Optionally, the provisional image displayer stops an update of the image data while the one frame worth of pixel-image signals, generated by the still image exposure, is read over the two field interval.

BRIEF DESCRIPTION OF THE DRAWINGS

The present invention will be better understood from the description of the preferred embodiments of the invention set forth below together with the accompanying drawings, in which.

DESCRIPTION OF THE PREFERRED EMBODIMENTS

Hereinafter, the preferred embodiments of the present invention are described with reference to the attached drawings.

Figure 1:
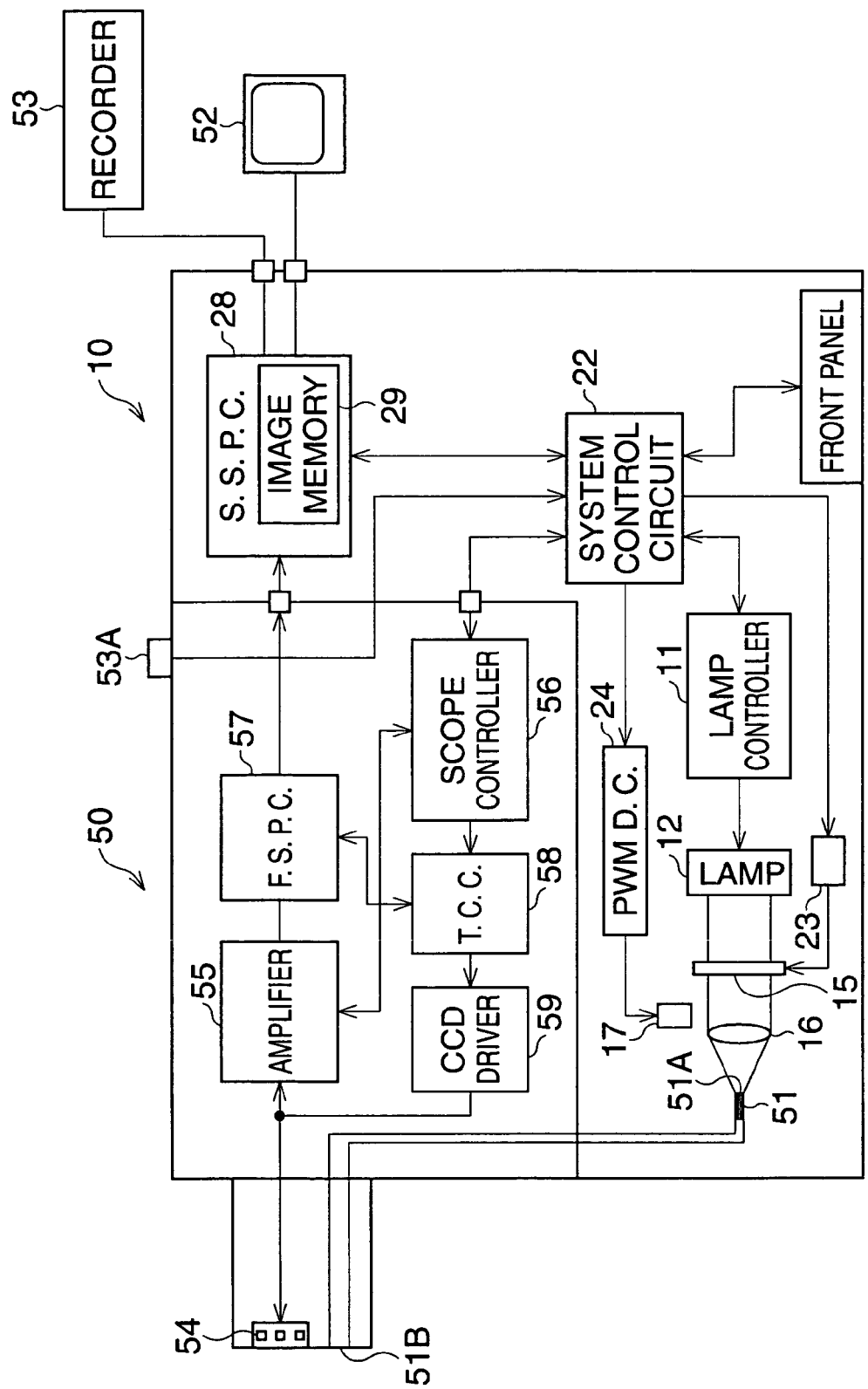
FIG. 1 is a block diagram of an electronic endoscope according to a first embodiment.

FIG. 1 is a block diagram of an electronic endoscope according to the first embodiment.

The electronic endoscope has a video-scope 50 with a CCD 54, and a video-processor 10 that has a lamp 12 and processes image-pixel signals read from the CCD 54. The video-scope 50 is detachably connected to the video-processor 10; and a monitor 52 and a recorder 53 that records a still image are connected to the video-processor 10.

When a lamp switch button (not shown) is turned ON, a lamp controller 11 supplies electric power to the lamp 12 so that the lamp 12 radiates illuminating light. Light emitted from the lamp 12 enters the incidence surface 51A of a light-guide 51 via a rotary shutter 15 and a collecting lens 16. The light-guide 51 is constructed of a fiber-optic bundle for directing the light to a tip end of the video-scope 10. The light exits from the end portion 51B of the light-guide 51, and illuminates an observed object via a diffusion lens (not shown).

Light, reflected on the object, reaches the CCD 54 via an objective lens (not shown), so that an object image is formed on the photo-sensitive area of the CCD 54. A color filter, checkered by four color elements of Yellow (Y), Magenta (M), Cyan (C), and Green (G), is arranged on the photo-receiving area such that the four color elements are opposite to pixels arranged in the photo-sensitive area. Based on the light passing through each color element, analog image-pixel signals are generated by the photoelectric transformation effect. The generated image-pixel signals are read from the CCD 54 at regular time intervals in accordance with clock pulse signals output from a CCD driver 54. A timing control circuit 58 in the video-scope 50 adjusts an output-timing of the clock pulse signals.

The CCD 54 is an interline-transfer CCD, and as for the color imaging method using an on-chip color filter, the so called "color difference lines sequential system" is applied. Therefore, while displaying a movie image, the photo-generated charges in pixels neighboring each other are mixed, and odd-field image-pixel signals and even-field image-pixel signals are alternately read from the CCD 54. The NTSC (or PAL) standard is herein applied as the TV standard, accordingly, the odd or even field image-pixel signals are read from the CCD 54 at a $\frac{1}{60}$ (or $\frac{1}{50}$) second time interval, and are then fed to an amplifier 55. The image-pixel signals are amplified in the amplifier 55 and are subjected to given processes in a first signal processing circuit 57. The processed image-pixel signals are fed to a second signal processing circuit 28.

In the second signal processing circuit 28, various processes, such a gamma correction process, a white balance process, and soon, are carried out on the image-pixel signals, so that digital image signals are generated and temporarily stored in an image memory 29 as digital image data. The digital image signals are read from the image memory and video signals such as NTSC signals are output to the monitor 52 at a given timing, thus an observed image is displayed on the monitor 52 as a movie image.

On the other hand, when displaying a still image on the monitor 52 and recording the still image in the recorder 53 by depressing a freeze button 53A on the video-scope 50, a one-time reading process, wherein one frame worth of image-pixel signals is generated by a one-time exposure, is performed. When electric charges are accumulated by a one-time exposure, image-pixel signals corresponding to an odd-line in the pixel-array are read from the CCD 54 over one-field reading interval, next, image-pixel signals corresponding to an even-line in the pixel array are read from the CCD 54 over one-field reading interval. One field worth of odd-line image-pixel signals and one field worth of even-line image-pixel signals are respectively fed to the amplifier 55, the first signal processing circuit 57, and the second signal processing circuit 28. Then, odd-field image signals and even-field image signals are respectively output to the monitor 52. Also, one field worth of odd-line image-pixel signals and one field worth of even-line image-pixel signals, which are processed in the second signal processing circuit 28, are fed to the recorder 53 as still image data.

A system control circuit 22 including a CPU (not shown) controls each circuit in the video-processor 10, and outputs control signals to the lamp controller 11, the second signal processing circuit 28, and so on. A timing control circuit, provided in the video-processor 10 (not shown), outputs clock pulse signals to each circuit in the video-processor 10 to adjust a process-timing, and outputs synchronous signals which are added to the video signals, to the second signal processing circuit 28. The system control circuit 22 controls an output-timing of the clock pulse signals fed to each circuit. For example, the system control circuit 22 adjusts an output-timing of clock pulse signals, which are output to the image memory 28 in accordance with the operation of the freeze button 53A to renew or rewrite image data, and adjusts an output-timing of clock pulse signals, which are output from the CCD driver 59 to drive the CCD 54.

A scope controller 56, provided in the video-scope 50, controls the first signal processing circuit 55 and the timing control circuit 58. The timing control circuit 58 outputs driving signals to the CCD driver 59 in accordance with the control signals output from the scope controller 56. Thus, the reading process of the image-pixel signals is controlled. When the video-scope 50 is connected to the video-processor 10, data are transmitted between the video-scope 50 and the video-processor 10.

The rotary shutter 15 is attached to a motor (not shown), and rotates at a constant speed on the basis of driving signals fed from a motor driver 23. A chopper 17, which shades or blocks the light to be directed to the end portion of the video-scope 50, is provided between the rotary shutter 15 and the collecting lens 16, and has a DC solenoid (herein, not shown). The chopper 17 motions in accordance with a series of pulse signals fed from a PWM driving circuit 24.

Figure 2:
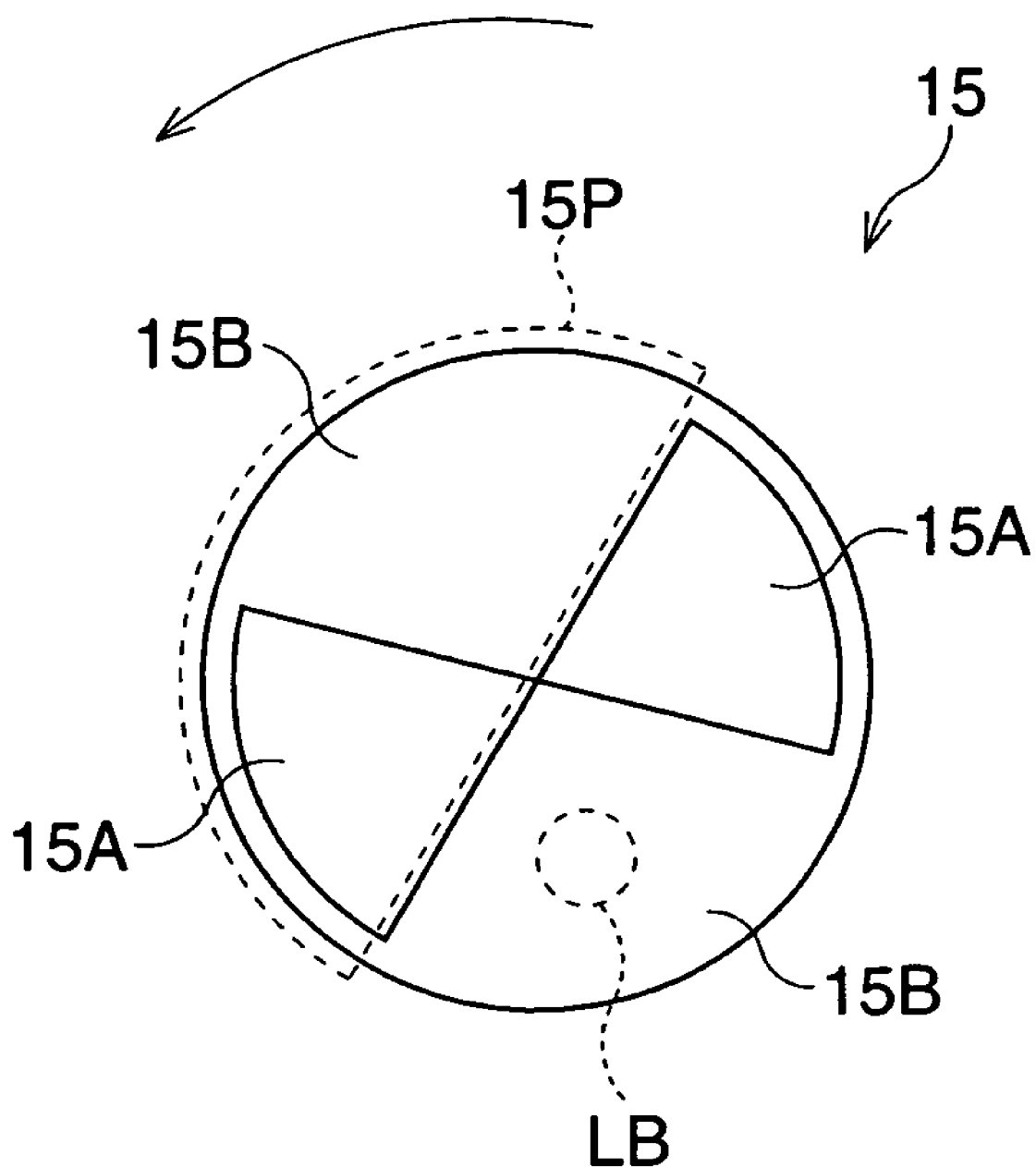
FIG. 2 is a plan view of a rotary shutter.
Figure 3:
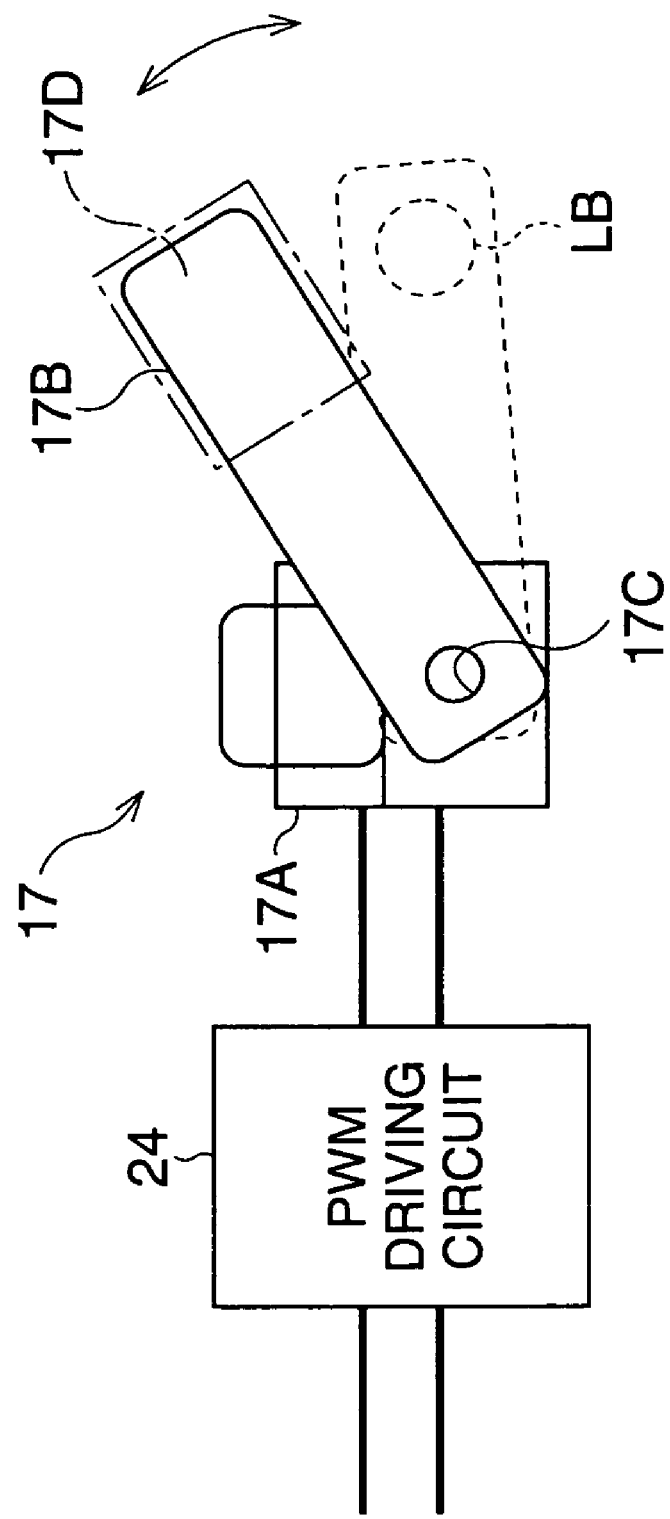
FIG. 3 is a plan view of a chopper.

FIG. 2 is a plan view of the rotary shutter 15. FIG. 3 is a plan view of the chopper 17.

The rotary shutter 15 is constructed of an aperture 15A that passes the light from the lamp 12 and a shading portion 15B that shades or shields the light. The aperture 15A is formed such that a pair of arc-shaped holes is opposite to each other. The rotary shutter 15 rotates by one-rotation in one-frame reading interval ($=\frac{1}{30}$ or $\frac{1}{25}$ second). Therefore, the half-circle 15P of the rotary shutter 15 corresponds to one-field reading interval ($=\frac{1}{60}$ or $\frac{1}{50}$ second). While the rotary shutter 15 rotates by a half-rotation, the aperture 15A and shading portion 15B pass the light-path of the light emitted from the lamp 12, in turn. Thus, an exposure interval and a shading interval alternately occur in one-field reading interval, which functions like an electronic shutter.

When displaying and recording the still image, one frame worth of image-pixel signals is obtained by light passing through one aperture 15A, namely, by rotating the rotary shutter 15 by a half-rotation. Then, the obtained one frame worth of image-pixel signals is read from the CCD 54 over the one-frame reading interval ($=\frac{1}{30}$ or $\frac{1}{25}$ second). Since the other aperture 15A passes the light-path for the remaining interval ($=\frac{1}{60}$ or $\frac{1}{50}$ second), the chopper 17 moves so as to block the illuminating light when the other aperture 15A passes the light-path.

In FIG. 3, the non-shading position of the chopper 17, which enables light to pass through one arc-shaped hole of the aperture 15A, is shown by a solid line, whereas the shading position of the chopper 17, which blocks the light when the other arc-shaped hole of aperture 15A passes the light-path, is shown by a broken line. The chopper 17 is a pivot-type solenoid, and has a DC solenoid 17A and a plate member 17B, which pivots around a center axis 17C. When the chopper 17 motions so as to shade the illuminating light, an end portion 17D of the plate member 17B covers the light-path or the aperture 15A of the rotary shutter 15. The PWM driving circuit 24 is a PWM controller, which outputs a sequence of pulse signals to the solenoid 17A.

Figure 4:
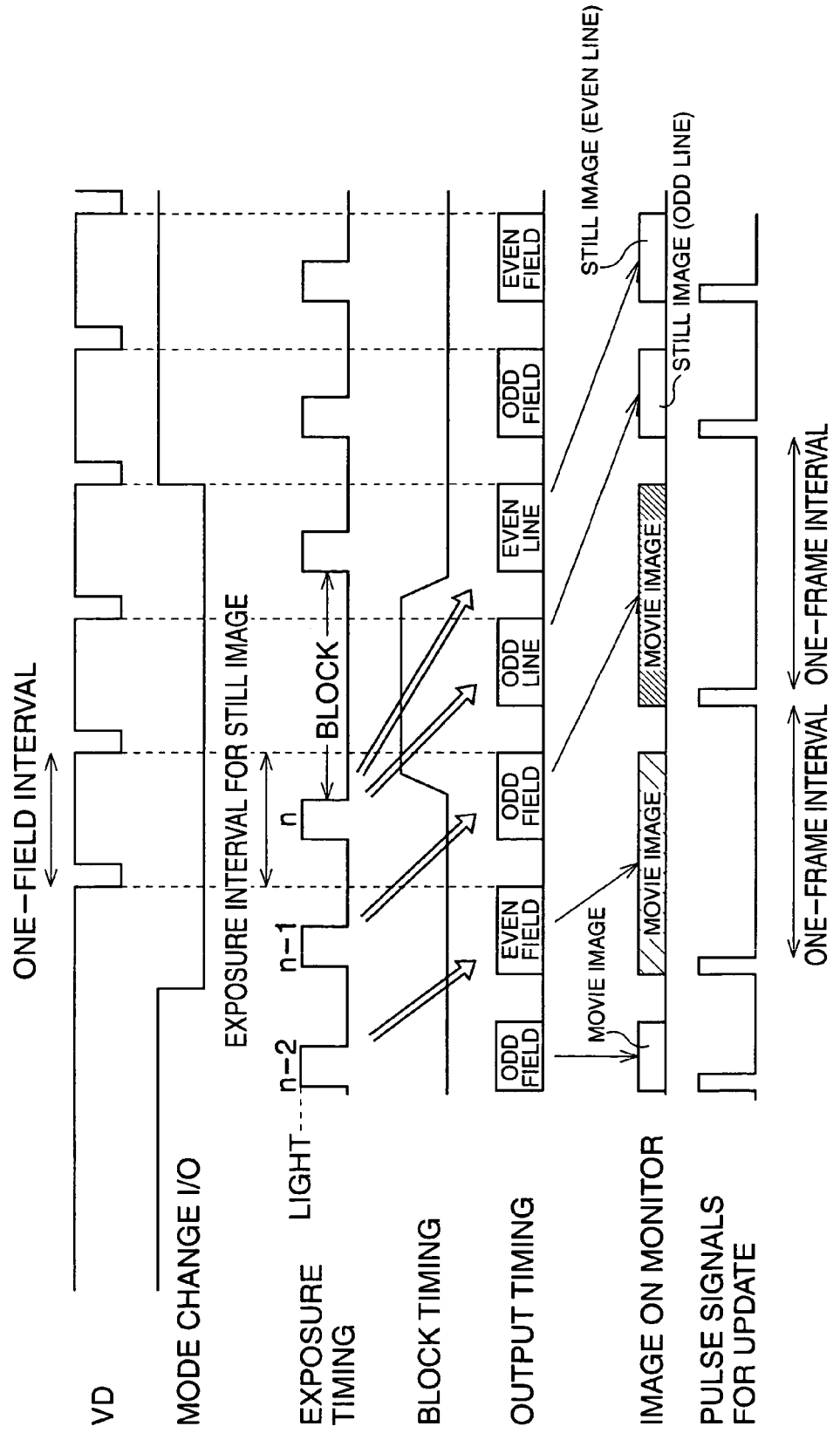
FIG. 4 is a view showing a timing chart of a recording process.

FIG. 4 is a view showing a timing chart of the recording process.

In a state where the freeze button 53A is not pressed, namely, a movie image is displayed, odd-field image-pixel signals and even-field image-pixel signals are alternately read from the CCD 54 at a $\frac{1}{60}$ (or $\frac{1}{50}$) of a second interval while mixing adjacent pixel signals, as described above. Since the CCD 54 is an interline type CCD, the photo-generated charges, which are accumulated by a given exposure-timing, are read in the next exposure-timing. For example, image-pixel signals, which are accumulated at "n−1" of the exposure-timing and correspond to the even-field, are read from the CCD 54 at "n" of the exposure-timing, as shown in FIG. 4. Clock pulse signals, which update the image data in the image memory 29, are output to the image memory 29 at $\frac{1}{60}$ (or $\frac{1}{50}$) time interval.

When the freeze button 53A is pressed to start recording a still image, all pixel signals, which are obtained during a one-time exposure time (in FIG. 4, the signals in the order of "n"), are read from the CCD 54 over a one-frame reading interval. Concretely, odd-line image-pixel signals and even-line image-pixel signals are read from the CCD 54, in turn, over two field intervals. During the reading of all image-pixel signals, the chopper 17 motions to block the illuminating light.

Further, when the recording process is performed, the output-interval of the clock pulse signals for update is changed from one-field interval to two-field (one-frame) intervals. The two-field intervals are based on pulse signals "SP", which are output at an exposure-time just before an exposure-time for recording the still image. Consequently, the odd-field image-pixel signals and the even-field image-pixel signals are respectively used to display the observed image over two field intervals. An observed image, formed by the odd-field image-pixel signals, is displayed for 1/30 (or 1/25) of a second, and an observed image, formed by the even-field image-pixel signals, is also displayed for 1/30 (1/25) of a second. After the one frame worth of image-pixel signals (odd-line image-pixel signals and even-line image-pixel signals) are read from the CCD 54, the interval of the update returns to one field interval.

Figure 5:
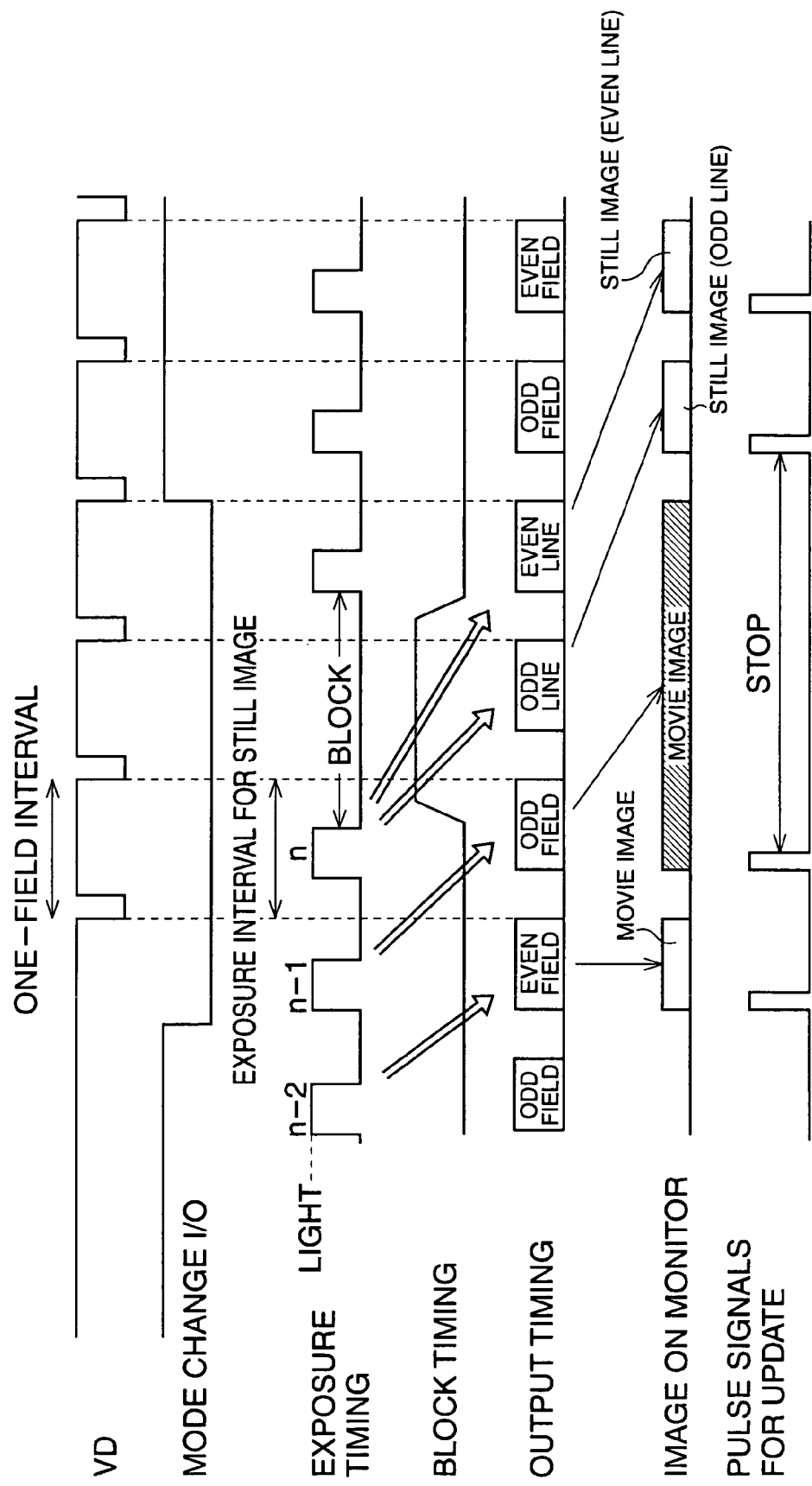
FIG. 5 is a view showing a timing chart of a recording process according to a second embodiment.

With reference to FIG. 5, the second embodiment is explained. The second embodiment is different from the first embodiment in that image data is not renewed while recording the still image.

FIG. 5 is a view showing a timing chart of a recording process according to the second embodiment.

When the recording process is started by depressing the freeze button 53A, as shown in FIG. 5, clock pulse signals for update are not output to the image memory 29 over two-field intervals. Then, odd-field image-pixel signals, obtained by an exposure just before the exposure for recording the still image, are used to display the observed image until the one frame worth of image-pixel signals for the still image is read from the CCD 54.

Finally, it will be understood by those skilled in the arts that the foregoing description is of preferred embodiments of the device, and that various changes and modifications may be made to the present invention without departing from the spirit and scope thereof.

The present disclosure relates to subject matter contained in Japanese Patent Application No. 2005-056979 (filed on Mar. 2, 2005), which is expressly incorporated herein, by reference, in its entirety.

The invention claimed is:

1. An electronic endoscope, comprising:
   a light source that radiates illuminating light;
   a movie-image processor that alternately reads odd-field image-pixel signals corresponding to an odd-field and even-field image-pixel signals corresponding to an even-field to generate a movie-image;
   a still-image processor that alternately reads odd-line image-pixel signals and even-line image-pixel signals over two field intervals to generate a still image on the basis of one frame worth of image-pixel signals generated by a one-time still image exposure, the illuminating light being blocked for a latter field interval in the two field intervals;
   an image change processor that switches between an operation of said movie-image processor for displaying the movie-image and an operation of said still-image processor for displaying the still-image; and
   a provisional image displayer that displays a provisional image on the basis of at least one of odd-field image-pixel signals and even-field image-pixel signals that are obtained by an exposure before the still image exposure for recording a still image, while said still-image processor reads the odd-line and even-line image-pixel signals over the two field intervals,
   wherein, when the operation of the still-image processor is started, the provisional image displayer displays, in order, a first provisional image based on even-field image-pixel signals that are obtained by an exposure before the still image exposure and subsequently a second provisional image based on odd-field image-pixel signals that are obtained by an exposure before the still image exposure, until the still-image processor finishes reading the odd-line and even-line image-pixel signals over the two field intervals.

2. The electronic endoscope of claim 1, further comprising:
   a rotary shutter that has an aperture and a shading portion that are formed so as to alternately pass and block the illuminating light, and that rotates to adjust an exposure-time.

3. The electronic endoscope of claim 1,
   wherein one field worth of image-pixel signals are temporarily stored in a memory as image data and are updated in each filed interval, and
   wherein said provisional image displayer changes an update interval of the image data from one field interval to two field intervals when the performance of the still image processor is started.

4. The electronic endoscope of claim 1,
   wherein one field worth of image-pixel signals are temporarily stored in a memory as image data and are updated in each filed interval, and
   wherein said provisional image displayer stops an update of the image data while the one frame worth of pixel-image signals, generated by the still image exposure, is read over the two field intervals.

5. An apparatus for displaying an observed image associated with an electronic endoscope, comprising:
   a still-image processor that alternately reads odd-line image-pixel signals and even-line image-pixel signals over two field interval to generate a still image on the basis of one frame worth of image-pixel signals generated by a one-time still image exposure, illuminating light being blocked for a latter filed interval in the two field interval;
   an image change processor that switches a performance of a movie-image processor for displaying a movie-image and a performance of said still-image processor for displaying the still-image; and
   a provisional image displayer that displays a provisional image on the basis of at least one of odd-field image-pixel signals and even-field image-pixel signals that are obtained by an exposure before the still image exposure for recording the still-image, while said still-image processor reads the odd-line and even-line image-pixel signals over the two field intervals,
   wherein, when the performance of the still-image processor is started, the provisional image displayer displays, in order, a first provisional image based on even-field image-pixel signals that are obtained by an exposure before the still image exposure and subsequently a second provisional image based on odd-field image-pixel signals that are obtained by an exposure before the still image exposure, until the still-image processor finishes reading the odd-line and even-line image-pixel signals over the two field intervals.

* * * * *